United States Patent [19]

Littrell

[11] Patent Number: 5,176,652
[45] Date of Patent: * Jan. 5, 1993

[54] HEMOSTASIS VALVE

[75] Inventor: Perry K. Littrell, Miami Lakes, Fla.

[73] Assignee: Cordis Corporation, Miami Lakes, Fla.

[*] Notice: The portion of the term of this patent subsequent to Aug. 20, 2008 has been disclaimed.

[21] Appl. No.: 692,187

[22] Filed: Apr. 26, 1991

Related U.S. Application Data

[63] Continuation of Ser. No. 455,956, Dec. 22, 1989, Pat. No. 5,041,095.

[51] Int. Cl.⁵ .......................................... A61M 25/00
[52] U.S. Cl. .................................. 604/167; 604/256; 137/849; 251/149.1
[58] Field of Search ............... 604/167, 169, 247, 256, 604/237; 251/149.1; 138/849

[56] References Cited

U.S. PATENT DOCUMENTS 4,000,739  1/1977  Stevens .
4,610,665  9/1986  Matsumoto et al. .
4,626,245  12/1986  Weinstein .
4,673,393  6/1987  Suzuki et al. .
4,798,594  1/1989  Hillstead .
4,895,346  1/1990  Steigerwald .
5,000,745  3/1991  Guest et al. .
5,041,095  8/1991  Littrell ............................... 604/167

Primary Examiner—Stephen C. Pellegrino
Assistant Examiner—Ralph A. Lewis
Attorney, Agent, or Firm—Gerstman & Ellis, Ltd.

[57] ABSTRACT

A hemostasis valve comprises a housing defining a passage therethrough adapted to receive an elongated member such as a catheter in hemostatically sealed condition. An elastic gasket valve is carried in the housing having slit means capable of permitting the elongated member to extend through the housing and the gasket member in hemostatically sealed condition. By this invention the gasket member defines a pair of opposed sides with a first slit extending inwardly of the gasket member from one of the opposed sides. A second slit extends inwardly of the gasket member from the other of the opposed sides. Both of the slits are of a shape defining a plurality of radii extending from a common origin. The first and second slits extend inwardly at a depth to engage but not to intersect each other, and the radii of the first slit each define an angle of at least 10° to each of the radii of the second slit at points of engagement. By this, an improved hemostasis valve is provided.

4 Claims, 2 Drawing Sheets

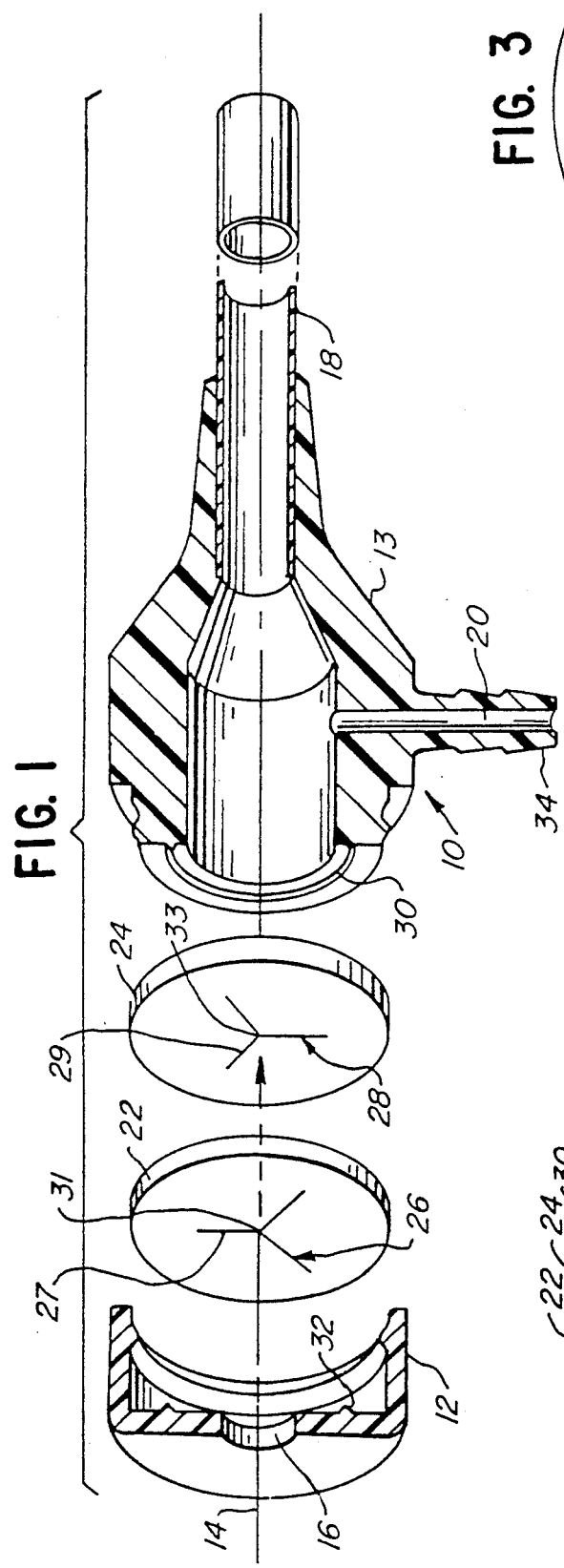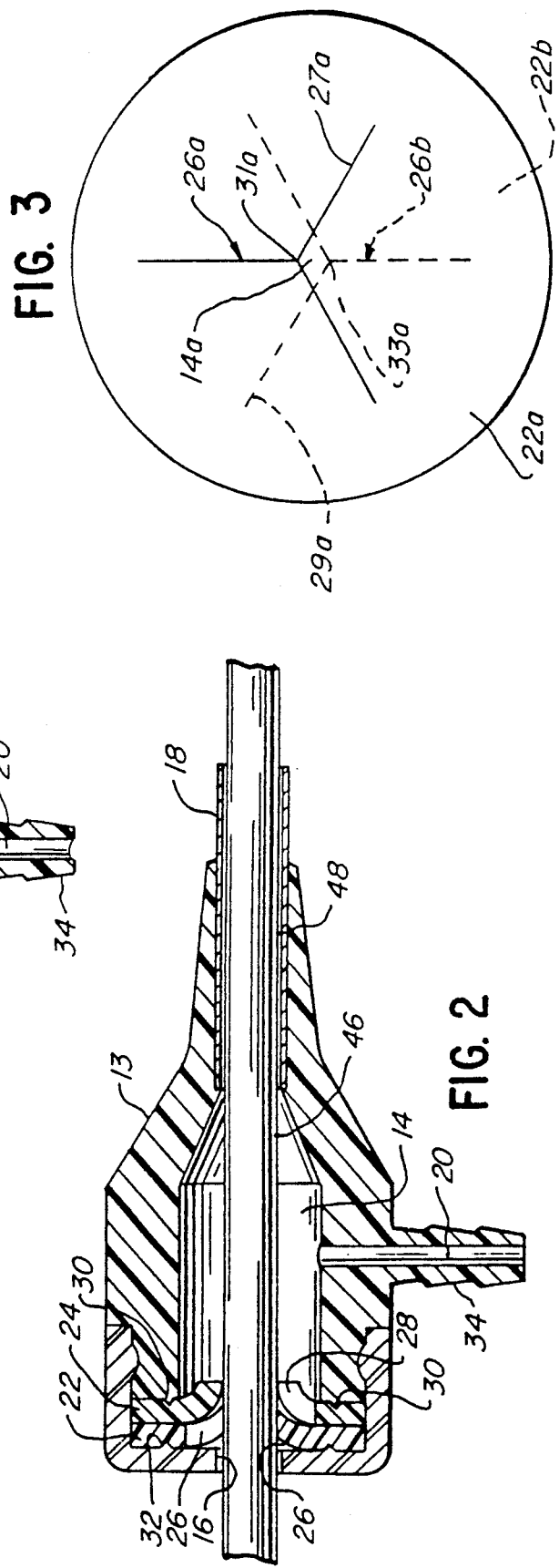

HEMOSTASIS VALVE

RELATED APPLICATION

This application is a continuation of U.S. application Ser. No. 455,956, filed Dec. 22, 1989, now U.S. Pat. No. 5,041,095.

BACKGROUND OF THE INVENTION

Hemostasis valves are used on hemostasis cannulas, such as catheter introducers which are presently in medical use for assisting in the insertion of angiographic catheters into the arterial system of a patient. Such hemostasis cannulas carry a rubber gasket hemostasis valve, which permits a catheter to pass through the gasket into the catheter introducer or other cannula while preventing blood leakage. Examples of patents which cover such hemostasis cannulas include Stevens U.S. Pat. No. 4,000,739, Weinstein U.S. Pat. No. 4,626,245, Matsumoto et al. U.S. Pat. No. 4,610,665, and Hillstead U.S. Pat. No. 4,798,594 among others.

In accordance with this invention, an improved hemostasis valve is provided in which a novel configuration is provided in the elastic gasket of the hemostasis valve. This configuration provides improved performance, including easy catheter advancement coupled with good sealing, to prevent the back leakage of blood when the cannula, on which the hemostasis valve is carried, is in communication with an artery, whether or not a catheter is extending through the valve.

DESCRIPTION OF THE INVENTION

In this invention a hemostasis valve is provided, typically being carried on the proximal end of catheter introducer cannula or the like. The valve of this invention comprises a housing defining a passage therethrough which is adapted to receive an elongated member such as a catheter in hemostatically sealed condition. Elastic gasket means are provided, being carried in the housing. The gasket means defines slit means capable of permitting such elongated members extending through the housing to also extend through the gasket means to provide the above-mentioned hemostatically sealed condition.

In accordance with this invention the gasket means defines a pair of opposed sides. A first slit extends inwardly of the gasket means from one of the opposed sides. The first slit is of a shape which defines a plurality of radii extending from a common origin.

A second slit extends inwardly of the gasket means from the other of the opposed sides. The second slit is also of a shape defining a plurality of radii extending from a common origin.

The first and second slits extend inwardly to a depth to engage but not intersect each other. By this it is meant that a catheter or the like can extend through the hemostasis valve through first one slit and then through the other slit without having to break through any of the material of the gasket means. However, the respective first and second slits do not intersect each other because they do not occupy any common plane that is perpendicular to the gasket axis. From the axial perspective, the dimension perpendicular to the gasket faces, the first slit ends and immediately the second slit begins, since they are engaging each other but not intersecting each other. There is no overlap, and no intervening, blocking gasket material.

The radii of the first slit each define an angle of at least 10 degrees to each of the radii of the second slit at their points of engagement. Preferably the angle is about 30° to 80°.

Also preferably, in the hemostasis valve of this invention the elastic gasket means comprises a pair of separate elastic gaskets, abutting along major faces. One of these gaskets defines the first slit extending completely therethrough, while the other of the gaskets defines the second slit extending completely therethrough.

While the first and second slits may be in coaxial relation to each other, they may also be in a relationship in which the first and second slits define separate, spaced axes. This latter situation is generally preferred, because the separate, spaced axial relation eliminates a tiny flow channel for pressurized blood flow along any common axis of the first and second slits.

While the radii of at least one of the first and second slits, and typically both, may define planar slit portions extending in essentially perpendicular relation between the opposed sides, it is also possible that the radii of at least one of the first and second slits may define helical section-shaped slit portions extending between the opposed sides in the manner of the Hillstead U.S. Pat. No. 4,798,594. If desired, one of the pair of separate, abutting elastic gaskets may have radii defining planar slit portions, while the other of the gaskets defines helical section-shaped slit portions, or both may be helical, or both may be planar and essentially perpendicular.

Preferably, each of the first second slits define three equiangularly extending radii, particularly with the adjacent first and second slits defining angles of about 60° to each other so that the respective radii of the first and second slits are in substantial angular relation to each other.

DESCRIPTION OF DRAWINGS

In the drawings, FIG. 1 is an exploded, fragmentary partially cut away view of one embodiment of a catheter introducer of the invention;

FIG. 2 is a longitudinal, fragmentary sectional view of the assembled structure of FIG. 1, with a catheter carried in the catheter introducer and hemostasis valve; and FIG. 3 is an elevational view of the elastic gasket means of the catheter introducer of FIG. 1, separated from the remaining parts and enlarged, showing a modified embodiment of the invention.

DESCRIPTION OF SPECIFIC EMBODIMENTS

Figure 4:
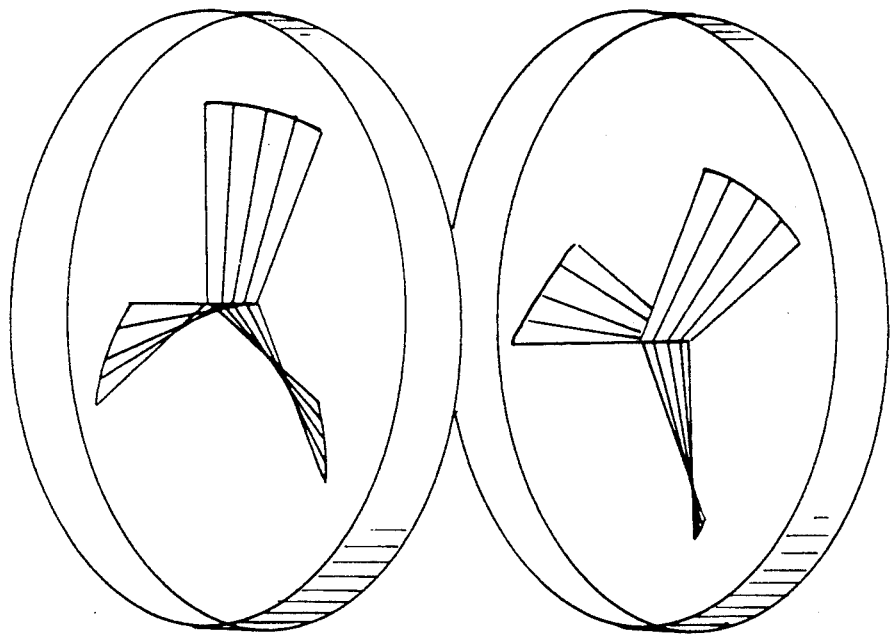
FIG. 4 is a view of a pair of gaskets used in accordance with the present invention, of an alternative embodiment.

Referring to FIGS. 1 and 2, the catheter introducer which carries the hemostasis valve of this invention defines a generally tubular housing 10 which connects with a snap-on cap 12 at its proximal end, which housing further defines a tapered portion 13 leading to a length of flexible cannula 18. The design and use of the catheter introducer may overall be the same as presently available catheter introducers which are in widespread medical use, but for the specific modifications and distinctions over the prior art as described herein.

Within housing 10 is a longitudinal passage generally designated by arrow 14 in FIG. 1. Housing 10 and flexible cannula 18 may be conveniently made of any one of a number of materials known to the prior art.

A pair of disk-like gaskets 22, 24 are enclosed within cap 12, for pressure securance between annular rib 30 of housing 13 and annular rib 32 of cap 12, and the surfaces that define them. Gaskets 22, 24 may be made of known elastomeric materials such as natural latex, silicone rubber or other commercially used materials.

As shown, both gaskets 22 and 24 define respective Y-slits 26, 28, each of the slits extending completely through their respective gasket disks 22, 24 and defining a plurality of respective radii 27, 29 extending from a common origin 31, 33, which origins 31, 33 are coaxially located on axis 14. While in this particular embodiment three radii 27, 29 are provided to each of disks 22, 24, the radii being equiangularly spaced from each other by angles of 120°, other arrangements and numbers of radii may be used as well, ranging preferably from 2 to 4 radii in each disk.

As shown in FIG. 2, disks 22, 24 are held with major faces in compressed, abutting relation. The respective slits 26, 28 thus abut each other, but do not intersect each other, since, in their normal condition as mounted within the catheter introducer, as one moves axially along axis 14, slit 26 ends as slit 28 begins, so that no portion of the respective slits occupy a common plane.

Also, from FIG. 1 it can be seen that the radii 29 of slit 28 each define an angle of essentially 60° to the radii 27 of the adjacent slit 26. It is generally preferred for the angle between the respective, adjacent radii, 27, 29 to be approximately the maximum possible. That maximum is 60° in the embodiment shown since, in the situation where a 60° angle between radii 29 and adjacent radii 27 exists, each radius 29 extends outwardly midway between the adjacent radii 27 positioned on each side thereof.

In the situation where each slit 26, 28 defines four outwardly extending, equiangularly spaced radii, the maximum and preferred angle between the radii of the respective, abutting gaskets 22, 24 would be 45°.

As previously stated, it is also contemplated that slits 26, 28 may be of differing numbers of radii. For example, one of the slits may be of chevron shape, having two radii, while the other of disks 22, 24 may define a slit of 3 or 4 radii, either equiangularly distributed or not as may be desired.

In the structure of FIGS. 1 and 2, slits 26, 28 define planar slit portions extending in generally perpendicular relation between the opposed sides or major faces of the gaskets, as shown. The opposed major faces are those faces which are perpendicular to axis 14. However, alternatively, gaskets 22, 24 may define slits which, in turn, define helical section-shaped slit portions extending between the opposed sides, as described and claimed in the previously cited Hillstead U.S. Pat. No. 4,798,594, the disclosure of such patent being incorporated by reference herein. This embodiment is illustrated in FIG. 4. If such helically shaped slits 26, 28 are used, the angular relationships described above relate to the respective abutting major faces of gaskets 22, 24 and the respective radial slit lines found thereon as defined by the respective slits 26, 28. If desired, one of gaskets 22, 24 may be of the design covered by the above cited Hillstead patent, and the other may define a slit having planar, perpendicular slit portions.

Slits 26, 28 as described above permit relatively unobstructed passage of a catheter 46 therethrough, with the respective gaskets 22, 24 providing improved sealing against the back flow of blood through cannula 18. Nevertheless, when catheter 46 is not in position within cannula 18 and housing 10, the respective slits 26, 28 close, and continue to provide good sealing against the back flow of blood.

Cap 12 defines a centrally located aperture 16 which is generally positioned coaxially with gaskets 22, 24. Annular ridge 32 seals gasket 22 against the cap 12, while a second annular ridge 30, disposed on housing 10, acts to seal gasket 24. The interaction between the cap 12 and a housing 10 provides a pressure seal on the periphery of the two abutting gaskets which are also contributes to the efficacy of the sealing characteristics thereof.

In FIG. 2 catheter 46 is shown extending through gaskets 22, 24 and the bore 48 of cannula 18, to provide easy access for catheter 46 into the arterial system of a patient after emplacement of the catheter introducer that carries the valve or this invention.

Side port 34 extends laterally outwardly from housing 10 and defines a bore which communicates with the hollow interior of the housing. Side port 34 defines steps or annular projections on its outer surface to provide good connection with a plastic tube, to provide the usual functions of the well-known side port and tube in the present, commercially available catheter introducers.

Thus, the catheter introducer shown includes a hemostasis valve which is easy to manufacture, comprising preferably a pair of separate elastomer disks 22, 24 having the slits 26, 28 of the described shape and angular relation to each other, to provide improvements in fluid sealing. If desired, gaskets 22, 24 may be made of a single, integral piece, where there is no intersection of the respective slits 26, 28 in the longitudinal direction defined by axis 14.

Turning to FIG. 3, a pair of slightly modified gaskets 22a, 22b are disclosed. The respective gaskets are held together in abutting relation between a housing 10 and an end cap 12 in any conventional manner, such as that of FIGS. 1 and 2. However, as a distinction from the previous embodiment, the respective slits 26a, 26b define separate, spaced axes, which extend through origins 31a, 33a of the slit radii 27a, 29a. It is preferred for this spacing to be symmetrical, so that the origins 31a, 33a of the radii of the respective slits are equally spaced from the axes of the respective gaskets 22a, 22b, which generally remain in coaxial relationship along axis line 14a, which also defines the axis of the entire catheter introducer.

As stated above, this slit arrangement of FIG. 3 provides an added advantage in that it eliminates the pin hole-sized leakage line defined in the previous embodiment by the fact that the respective origins 31, 33 of slits 26, 28 are in coaxial relationship.

The above has been offered for illustrative purposes only, and is not intended to limit the scope of the invention of this application, which is as defined in the claims below.

That which is claimed is:

1. A catheter introducer including a hemostasis valve which comprises a housing defining a passage therethrough adapted to receive a catheter in hemostatically sealed condition; and elastic gasket means carried in said housing having slit means capable of permitting an elongated member extending through said housing to also extend through said gasket means, to provide said hemostatically sealed condition, the improvement comprising, in combination:

said elastic gasket means comprising a pair of separate round elastic gaskets, said separate elastic gaskets defining a pair of opposed outwardly facing sides, one side on each gasket, a first slit extending inwardly of said gaskets from one of said opposed sides, said first slit being of a shape defining a plurality of radii extending from a common origin; a second slit extending inwardly of said gaskets from the other of said opposed sides, said second slit being of a shape defining a plurality of radii extending from a common origin, one of said gaskets defining the first slit extending completely therethrough and the other of said gaskets defining the second slit extending completely therethrough, whereby said first and second slits extend inwardly of said gaskets at a depth to engage but not to intersect each other, each of the first and second slits defining a separate origin that is laterally spaced from the other origin, each of said origins being laterally spaced from the central axis of the round gasket, the radii of the first slit each defining an angle of at least 10° to each of the radii of the second slit at points of engagement.

2. The catheter introducer of claim 1 in which the radii of at least one of said first and second slits define planar slit portions extending in essentially perpendicular relation between said opposed sides.

3. The catheter introducer of claim 1 in which said first and second slits each define three equiangularly extending radii, and in which adjacent first and second slits define angles of about 60° to each other.

4. The catheter introducer of claim 1, in which the radii of at least one of said first and second slits define planar slit portions extending in essentially perpendicular relation between said opposed sides, and in which said first and second slits each define three equiangularly extending radii, and in which adjacent first and second slits define angles of about 60° to each other.

* * * * *